(12) United States Patent
Baek et al.

(10) Patent No.: US 9,808,743 B2
(45) Date of Patent: Nov. 7, 2017

(54) ROLL TYPE FILTER CLEANING APPARATUS

(71) Applicant: Samsung Electronics Co., Ltd., Suwon-si, Gyeonggi-do (KR)

(72) Inventors: Sang-hyun Baek, Hwaseong-si (KR); Tae-han Lee, Seoul (KR); Hyo-young Jeong, Seoul (KR); Young-ki Hahn, Seoul (KR); Soo-suk Lee, Suwon-si (KR); Youn-suk Choi, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 176 days.

(21) Appl. No.: 14/181,225

(22) Filed: Feb. 14, 2014

(65) Prior Publication Data

US 2015/0034134 A1 Feb. 5, 2015

(30) Foreign Application Priority Data

Jul. 30, 2013 (KR) ........................ 10-2013-0090422

(51) Int. Cl.
*B01D 29/07* (2006.01)
*A61M 1/36* (2006.01)

(52) U.S. Cl.
CPC ......... *B01D 29/073* (2013.01); *A61M 1/3633* (2013.01); *A61M 2205/7554* (2013.01)

(58) Field of Classification Search
CPC ........................................... A61M 2205/7554
See application file for complete search history.

(56) References Cited

U.S. PATENT DOCUMENTS

| | | | |
|---|---|---|---|
| 5,322,535 A | 6/1994 | Simms et al. | |
| 2006/0065596 A1 | 3/2006 | Kent et al. | |
| 2011/0000380 A1* | 1/2011 | Jamison | A47J 27/05 99/417 |
| 2011/0083563 A1* | 4/2011 | Branson | A47J 27/04 99/410 |

FOREIGN PATENT DOCUMENTS

| | | |
|---|---|---|
| KR | 10-0638980 B1 | 10/2006 |
| KR | 10-1113272 A2 | 4/2011 |

* cited by examiner

*Primary Examiner* — Michael Barr
*Assistant Examiner* — Jason Riggleman
(74) *Attorney, Agent, or Firm* — Leydig, Voit & Mayer, Ltd.

(57) ABSTRACT

Provided is a filter cleaning apparatus for cleaning a roll-type filter including a cleaning tank with a cavity for accommodating a cleaning solution, and a frame that is separable from the cleaning tank and is provided with a fixed portion for fixing a roll-type filter and a supporting portion for supporting weight of the roll-type filter, wherein the supporting portion includes a plurality of through holes through which the cleaning solution passes, and a plurality of supporting members for partially supporting a lower portion of the roll-type filter.

17 Claims, 10 Drawing Sheets

ROLL TYPE FILTER CLEANING APPARATUS

CROSS-REFERENCE TO RELATED APPLICATIONS

This application claims the benefit of Korean Patent Application No. 10-2013-0090422, filed on Jul. 30, 2013, in the Korean Intellectual Property Office, the entire disclosure of which is hereby incorporated by reference.

BACKGROUND OF THE INVENTION

1. Field

The present disclosure relates to filter cleaning apparatuses for cleaning a roll-type filter, and more particularly, to filter cleaning apparatuses that remove foreign substances or ionic substances remaining in a roll-type filter while minimizing damage to the roll-type filter.

2. Description of the Related Art

Filters are used to filter unwanted foreign substances or extract desired materials from a starting material.

In such a process of manufacturing a filter, unintended foreign substances or ionic substances may become trapped in the filter. According to the purpose of use, such foreign substances or ionic substances may need to be removed in some cases. For example, in a case of a blood separating filter for separating blood plasma from whole blood, certain ionic substances, when trapped in the filter, can lower the accuracy of the filter, and thus a separate cleaning process is required.

BRIEF SUMMARY OF THE INVENTION

Provided are filter cleaning apparatuses which have a simple structure, may clean a roll-type filter in a short period of time, and may minimize damage thereto.

Additional aspects will be set forth in part in the description which follows and, in part, will be apparent from the description, or may be learned by practice of the presented embodiments.

According to one embodiment of the present disclosure, a filter cleaning apparatus for cleaning a roll-type filter includes (i) a cleaning tank provided with a cavity for accommodating a cleaning solution, (ii) a frame that is separable from the cleaning tank and is provided with a fixed portion for fixing the roll-type filter and a supporting portion for supporting weight of the roll-type filter, wherein the supporting portion includes a plurality of through holes through which the cleaning solution passes, and a plurality of supporting members for partially supporting a lower portion of the roll-type filter.

The roll-type filter may be wound around a hollow shaft, and the fixed portion may be inserted into the hollow shaft so as to fix the roll-type filter.

The frame may further include a handle portion which protrudes toward the outside of the cleaning tank.

The supporting members may be disposed along a radial direction of the roll type filter so as to be separated from each other.

A distance between the supporting members may be approximately 5 mm to approximately 50 mm.

The supporting members may protrude toward the roll-type filter.

A protruding height of a supporting member may be approximately 5 mm to approximately 10 mm.

A width of a supporting member may be approximately 5 mm to approximately 10 mm.

Each of the supporting members may extend along in a circumferential direction relative to the roll-type filter.

The supporting members may be disposed along the circumferential direction of the roll-type filter so as to be separated from each other.

At least one of the cleaning tank and the frame may include a spacer so that a bottom surface of the cleaning tank and a lower surface of the supporting portion are separated from each other.

The cleaning tank may further include an outlet for discharging the cleaning solution.

The fixed portion may be detachably connected to the supporting portion.

The fixed portion may include a region comprising an upper diameter and lower diameter, wherein the upper diameter is smaller than the lower diameter.

The handle portion may be detachably connected to the fixed portion.

The filter cleaning apparatus may further include a cover which is disposed above the cavity.

The filter cleaning apparatus may further include an elastic member having a ring shape which is disposed between the cover and the cleaning tank.

The cover may be provided with a hole along at least a portion of an edge of the cover, suitable for injecting the cleaning solution. The cover may be provided with an opening and closing portion capable of obstructing the hole. The cover may have an inclined portion which is sloped toward the hole.

The filter may be a filter formed of glass fiber.

In the disclosed filter cleaning apparatus, the frame is disposed within the cleaning tank accommodating the cleaning solution so as to be separable from the cleaning tank, and the filter having a roll shape is disposed onto the frame to be fixed to and supported by the frame. Thus, damage to the filter may be minimized, and cleaning of large quantities of the filter may be performed within a short period of time.

In addition, the through holes and the supporting members are formed in the supporting portion for supporting the filter on the frame, and thus a cleaning solution may be uniformly supplied to the filter, thereby uniformly cleaning the filter as a whole.

Furthermore, the handle portion may be provided as part of the frame, allowing easy loading of the filter onto the frame. . Therefore, a cleaning solution may be smoothly supplied into the internal pores of the filter at the time of cleaning, and the filter may be easily moved to a separate drying apparatus from the cleaning tank after the cleaning.

BRIEF DESCRIPTION OF THE DRAWINGS

These and/or other aspects will become more readily apparent and appreciated from the following description of the embodiments, taken in conjunction with the accompanying drawings, in which.

DETAILED DESCRIPTION OF THE INVENTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the whole list of elements and do not modify the individual elements of the list.

Figure 1:
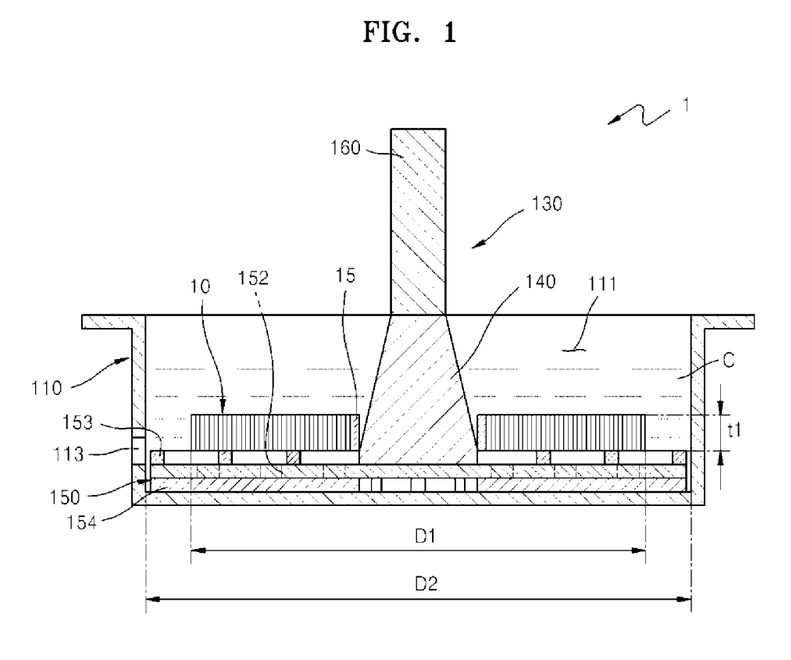
FIG. 1 is a schematic cross-sectional view illustrating an embodiment of the present disclosure where a roll-type filter is disposed in a filter cleaning apparatus.
Figure 2:
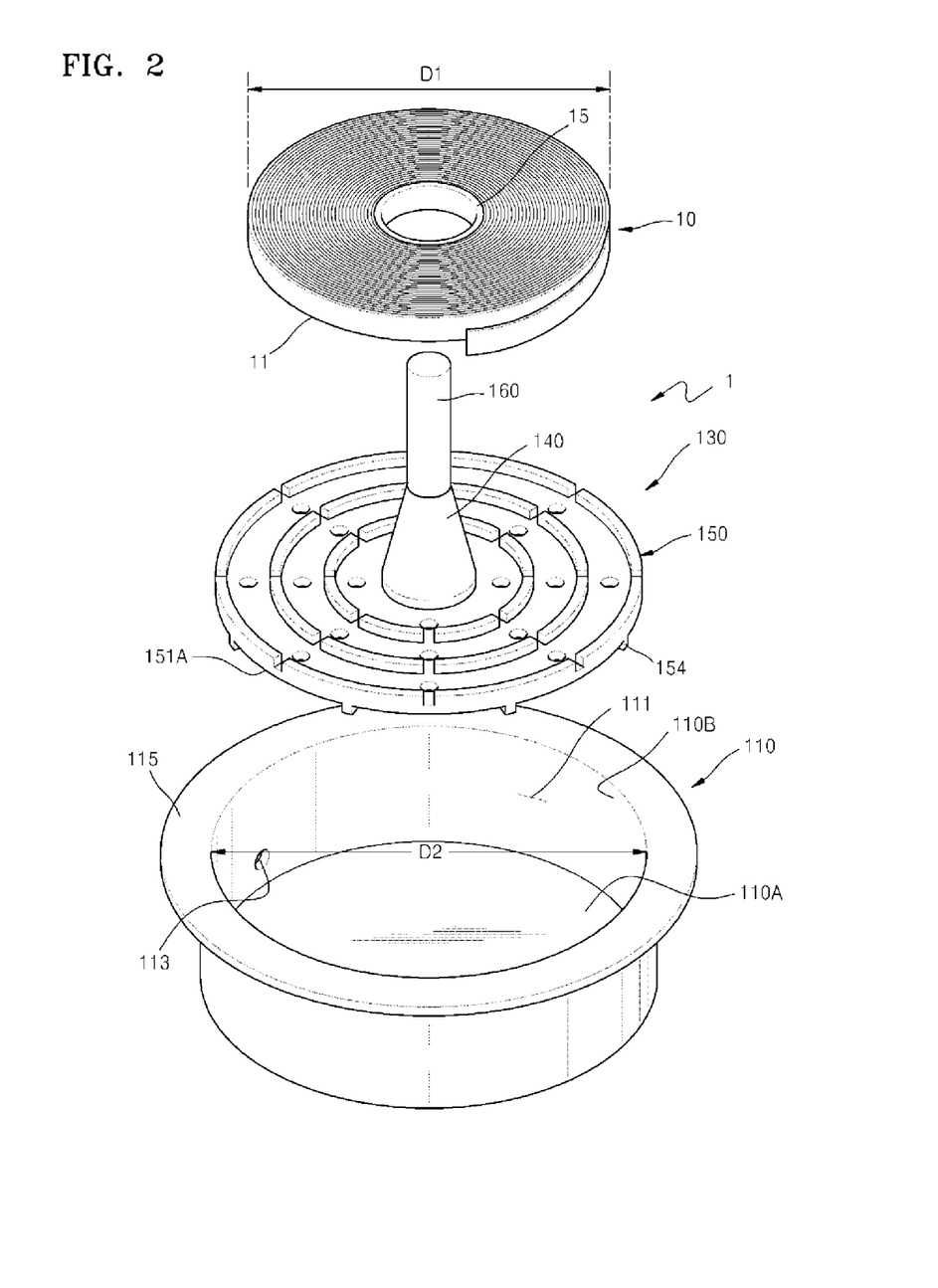
FIG. 2 is an exploded perspective view of the filter cleaning apparatus of FIG. 1.
Figure 3:
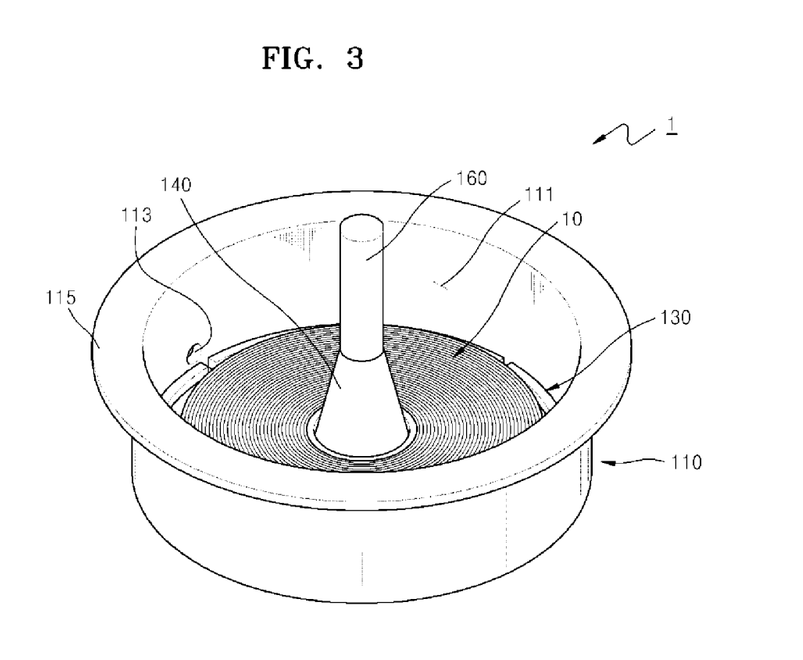
FIG. 3 is an assembled perspective view of the filter cleaning apparatus of FIG. 1.

FIG. 1 is a schematic cross-sectional view illustrating an embodiment of the present disclosure where a roll-type filter is disposed in a filter cleaning apparatus 1. FIGS. 2 and 3 are an exploded perspective view and an assembled perspective view of the filter cleaning apparatus 1 of FIG. 1, respectively.

Referring to FIG. 1, the filter cleaning apparatus 1 according to the current embodiment accommodates a cleaning solution C for cleaning a roll-type filter 10. A roll-type filter 10 is disposed in the filter cleaning apparatus 1 accommodating the cleaning solution C, and thus the cleaning solution C uniformly comes into contact with top, bottom, and side portions of the roll-type filter 10.

As illustrated in FIG. 2, the roll-type filter 10 is disposed in the filter cleaning apparatus 1, and thus the filter 10, having a considerable length, for example, a length of approximately 10 m to approximately 100 m, may be cleaned collectively. When a filter, instead of the roll-type filter 10, is individually cleaned, as the length of the filter increases, a cleaning time may be increased or the size of a cleaning apparatus may be increased. However, in the current embodiment, the roll-type filter 10 is cleaned as it is, and thus an increase in cleaning time and an increase in size of the cleaning apparatus at the time of cleaning may be minimized in spite of an increase in length of the roll-type filter 10.

As an example of the roll-type filter 10, the roll-type filter 10 may be wound around a hollow shaft 15. When the roll-type filter 10 is unwound, the whole length of the filter having a sheet shape may be approximately 10 m to approximately 100 m. However, the present disclosure is not limited thereto, and the whole length thereof may vary according to the diameter of the hollow shaft 15 and the number of windings of the roll-type filter 10 around the hollow shaft 15. Meanwhile, a width t1 of the roll-type filter 10 is approximately 10 mm to approximately 30 mm, and a diameter D1 of the roll-type filter 10 which is wound around the hollow shaft 15 may be approximately 100 mm to approximately 300 mm. In FIG. 2, an example of the roll-type filter 10 wound around the hollow shaft 15 is described. However, the present disclosure is not limited thereto, and a configuration may be employed in which only the roll-type filter 10 is wound without the hollow shaft 15.

The roll-type filter 10 may be a microporous hollow membrane roll-type filter 10 that is formed of glass fiber. Pores (not shown) within the roll-type filter 10 may have a diameter of approximately several pm to several mm, for example, approximately 1 μm to approximately 1 mm. The roll-type filter 10 may be used as a blood separating filter.

When the roll-type filter 10 is a membrane roll-type filter, the roll-type filter 10 is susceptible to be damage by external force. Thus, the roll-type filter 10 requires care so as not to be damaged. In the current embodiment, the roll-type filter 10 is cleaned by being immersed in the cleaning solution C, and thus the probability of the roll-type filter 10 being damaged may be remarkably decreased, as compared with a method of using a high-pressure fluid.

An objective of the current embodiment is to provide the filter cleaning apparatus 1 with a relatively simple structure and high detergency in order to clean the roll-type filter 10.

Referring to FIGS. 2 and 3, the filter cleaning apparatus 1 according to the current embodiment includes a cleaning tank 110 accommodating the cleaning solution C, and a frame 130 that is separable from the cleaning tank 110 and fixedly supports the roll-type filter 10. For convenience of description, the cleaning solution C is not illustrated in FIGS. 2 and 3.

The cleaning tank 110 is provided with a cavity 111 for accommodating the cleaning solution C therein. The size (diameter) of the cavity 111 may vary depending on a cleaning method and the type of roll-type filter 10. For example, a diameter D2 of the cavity 111 may be greater by approximately at least 5 cm than the diameter D1 of the roll-type filter 10 so that the cleaning solution C is not directly poured onto the roll-type filter 10 when the roll-type filter 10 is disposed in the cleaning tank 110. The height of the cavity 111 may vary depending on the height of the roll-type filter 10 and the cleaning method.

The cleaning tank 110 is provided with an outlet 113 for discharging the cleaning solution C. As illustrated in FIGS. 2 and 3, the outlet 113 may be formed in a side surface 110S of the cleaning tank 110. However, the present disclosure is not limited thereto, and the outlet 113 may be formed in a bottom surface 110A of the cleaning tank 110. Although not shown in the drawing, the bottom surface 110A of the cleaning tank 110 may include an inclined portion of which at least a part is sloped toward the outlet 113 so as to smoothly discharge the cleaning solution C.

A holder portion 115 may be formed outside the cleaning tank 110 so as to facilitate the transportation of the cleaning tank 110. The holder portion 115 is formed along a circumferential direction of the cleaning tank so as to protrude toward the outside as illustrated in FIGS. 2 and 3, but the present disclosure is not limited thereto.

At least a portion of the frame 130 is disposed within the cavity 111. The frame 130 is provided with a fixed portion 140 for fixing the roll-type filter 10, a supporting portion 150 for supporting the weight of the roll-type filter 10, and a handle portion 160 that protrudes toward the outside of the cleaning tank 110.

The roll-type filter 10 is wound around the hollow shaft 15, and may be fixed by inserting the fixed portion 140 into the hollow shaft 15. Thus, the roll-type filter 10 may be prevented from shifting, for example, in a horizontal direction, during a cleaning process or a transfer process.

The fixed portion 140 may include a region comprising an upper diameter and lower diameter, wherein the upper diameter is smaller than the lower diameter, so as to be easily fixed to the roll-type filter 10. For example, the fixed portion 140 may have a conical shape as illustrated in FIGS. 2 and 3.

Figure 4:
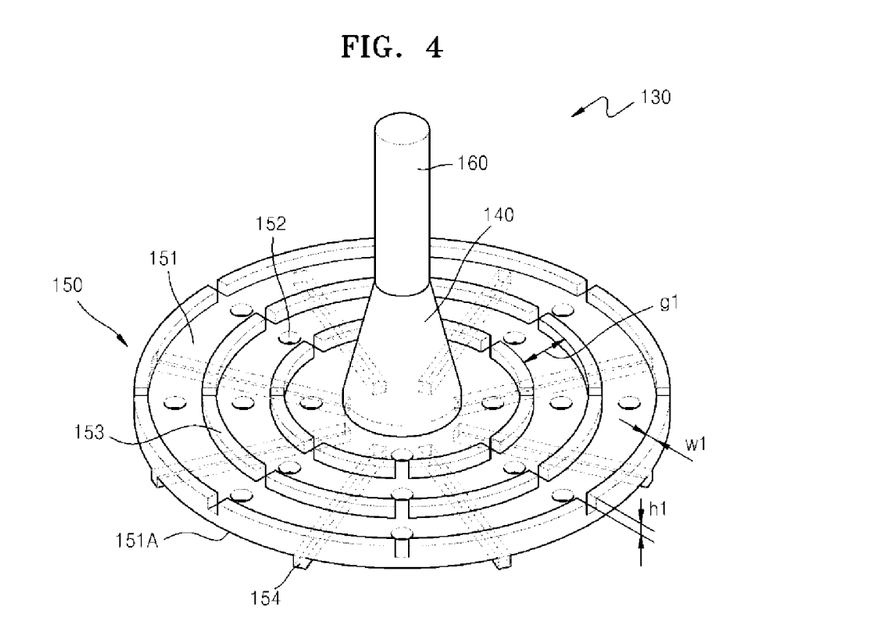
FIG. 4 is an enlarged perspective view of a frame of FIG. 2.

FIG. 4 is an enlarged perspective view of the frame 130 of FIG. 2. Referring to FIG. 4, the supporting portion 150 includes a base 151 for supporting the fixed portion 140, and the base 151 is provided with a plurality of through holes 152 and a plurality of supporting members 153. The base 151 may have a circular plate shape as a whole. However, the shape of the base 151 is merely an example, and may vary depending on the shape of the cavity 111 of the cleaning tank 110.

The plurality of through holes 152 provide a path through which the cleaning solution C accommodated in the cleaning tank 110 moves between an upper portion and a lower portion of the supporting portion 150. In particular, when the frame 130 moves within the cleaning tank 110 due to external force applied to the frame 130, the cleaning solution C can move through the through holes. Here, the external force may be provided by an operator. However, the present disclosure is not limited thereto, and the external force may be provided by a separate apparatus.

The plurality of supporting members 153 partially support a lower portion of the roll-type filter 10. The cleaning solution C is better able to moveto the lower portion of the roll-type filter 10, because the lower portion of the roll-type filter 10 is only partially supported by the plurality of supporting members 153. When the supporting members 153 entirely support the whole lower portion of the roll-type filter 10, the cleaning solution C is not likely to be supplied to the lower portion of the roll-type filter 10 due to the supporting members 153 coming into contact with the whole lower portion of the roll-type filter 10.

As an example in which the supporting members 153 partially support the lower portion of the roll-type filter 10, the supporting members 153 are disposed so as to be radially separated from each other relative to the roll-type filter 10 as illustrated in FIG. 4, and each of the supporting members 153 may extend along a circumferential direction.

The weight of the roll-type filter 10 may be distributed by disposing the supporting members 153 so as to be radially separated from each other relative to the roll-type filter 10. Thus, the roll-type filter 10 may be prevented from being damaged due to the weight thereof. However, when the roll-type filter 10 is formed of a material vulnerable to weight despite the distribution of the weight, a region of the roll-type filter 10 which comes into contact with the supporting members 153 may become damaged. In the current embodiment, the supporting members 153 are disposed so as to be tradially separated from each other relative to the roll-type filter 10, and each of the supporting members 153 is formed to extend along in a circumferential direction. The supporting members 153 are formed in such a manner, so that even though the roll-type filter 10 is damaged in contact regions with the supporting members 153, the damage of the roll-type filter 10 is limited to only some regions.

Figure 5:
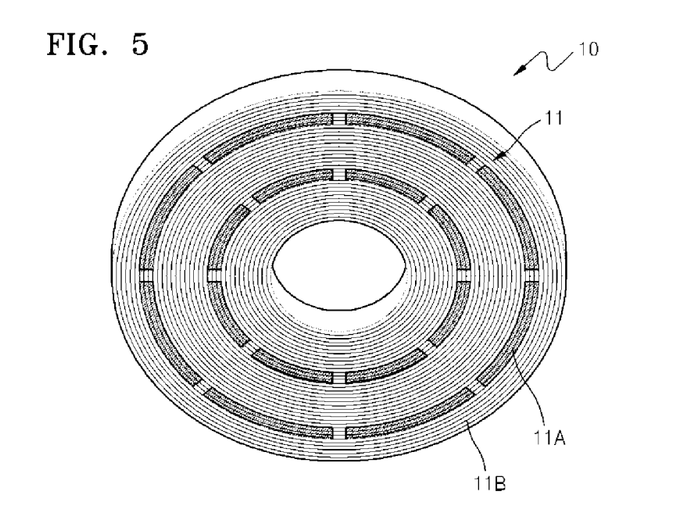
FIG. 5 is a perspective view of the bottom of a filter that is disposed in the filter cleaning apparatus of FIG. 2.

FIG. 5 is a perspective view of the bottom of the roll-type filter 10 that is disposed in the filter cleaning apparatus 1. Referring to FIG. 5, even though a bottom 11 of the roll-type filter 10 is damaged due to the arrangement and shape of the supporting members 153 (see FIG. 4), the damage is limited to only contact regions 11A that are formed along the circumferential direction. Accordingly, in the current embodiment, even though the roll-type filter 10 is damaged, the roll-type filter 10 may be unwound to remove only the damaged contact regions 11A, and then a remaining region 11B may be used as it is.

Referring back to FIG. 4, the supporting members 153 may be radially separated from each other at a distance g1 of approximately 5 mm to approximately 50 mm. When the distance g1 is less than 5 mm, portions of the supporting members 153 which may come into contact with the cleaning solution C may be relatively reduced, and thus the cleaning solution C may not be as likely to be smoothly supplied to the lower portion of the roll-type filter 10. Meanwhile, when the distance g1 exceeds 50 mm, a load may be concentrated on the contact regions 11A that come into contact with the supporting members 153, and the remaining region 11B, which does not contact with the supporting members 153, may hang due to the load. The hang of the remaining region 11B due to the load is associated with frictional force between the roll-type filters 10, and the degree of hang of the remaining region 11 B may vary depending on a material of the roll-type filter 10.

The supporting members 153 may be disposed so as to be separated from each other along the circumferential direction of the roll-type filter 10. Thus, the cleaning solution C may smoothly flow not only through the through holes 152 but also through a region between the supporting members 153 that are separated from each other along the circumferential direction.

The supporting members 153 may be formed to protrude toward the roll-type filter 10. Thus, the cleaning solution C may be more smoothly supplied to or discharged from the lower portion of the roll-type filter 10. By being smoothly discharged from the lower portion of the roll-type filter 10, the cleaning solution C may be prevented from being filled in the roll-type filter 10 due to surface tension. A height h1 and a width w1 of the protruding supporting member 153 may be set to a predetermined size. For example, the height h1 of the protruding supporting member 153 may be approximately 5 mm to approximately 10 mm, and the width w1 of the supporting member 153 may be approximately 5 mm to approximately 10 mm. Although FIG. 5 illustrates the distance g1 between the supporting members 153 and the width w1 of the supporting member 153 being the same as each other, the present disclosure is not limited thereto. The distance g1 and the width w1 may vary when necessary.

The supporting portion 150 may further include at least one spacer 154. The spacer 154 separates the bottom surface 110A (see FIG. 2) of the cleaning tank 110 and a bottom 151A of the supporting portion 150 from each other. A space is made between the bottom surface 110A of the cleaning tank 110 and the bottom 151A of the supporting portion 150 through the use of spacers 154, and thus the cleaning solution C may easily move in the lower portion of the supporting portion 150. The cleaning solution C moving in the lower portion of the supporting portion 150 may move to an upper portion of the supporting portion 150 through the through holes 152 and then reach the roll-type filter 10. On the contrary, the cleaning solution C moving in the upper portion of the supporting portion 150 may move to the lower portion of the supporting portion 150 through the through holes 152. In addition, the spacer 154 may prevent the cleaning solution C from being filled in the lower portion of the supporting portion 150 when discharging the cleaning solution C through the outlet 113 of the cleaning tank 110. In particular, when the outlet 113 is formed in the side surface 110B, the spacer 154 may be designed in such a manner that the roll-type filter 10 is disposed higher than the center of the outlet 113 as illustrated in FIG. 1. Thus, after the cleaning solution C is drained, the cleaning solution C of the cleaning tank 110 which has not been drained may be prevented from coming into contact with the roll-type filter 10. Although an example in which the spacers 154 are formed in the supporting portion 150 has been mainly described so far, the present disclosure is not limited thereto. The spacers 154 may also be formed in the cleaning tank 110 as long as it separates the supporting portion 150 and the cleaning tank 110 from each other. For example, although not shown in the drawing, the spacer 154 may be formed in the bottom surface 110A or the side surface 110B of the cleaning tank 110.

Figure 6A:
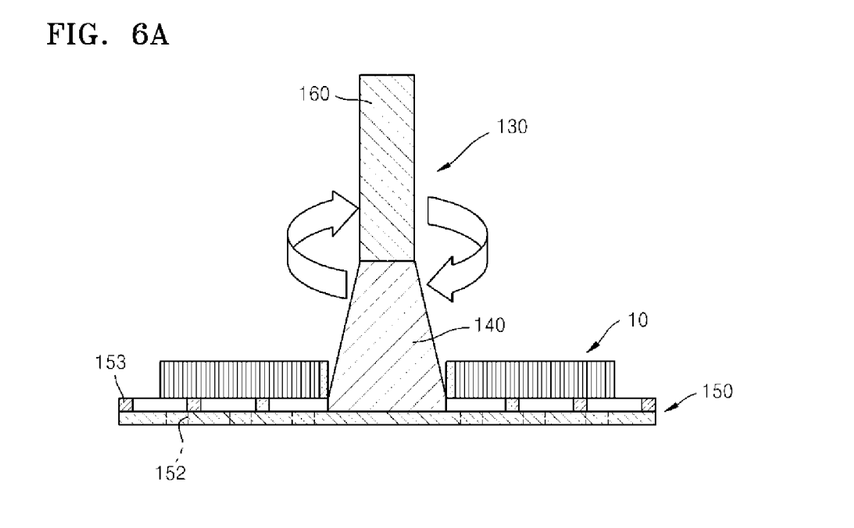
FIGS. 6A to 6C are schematic diagrams illustrating a use state of the frame according to an embodiment of the present disclosure.
Figure 6B:
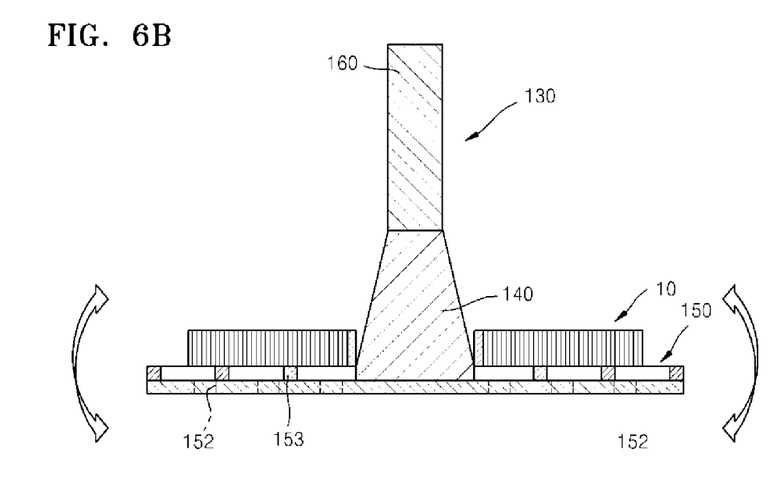
Figure 6C:
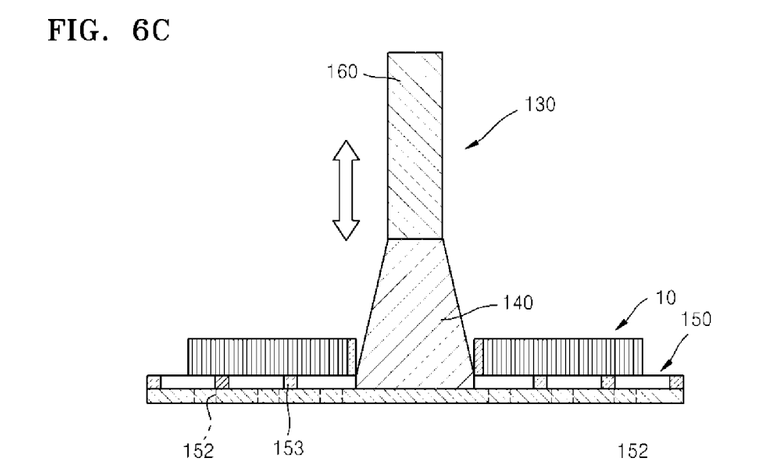

The handle portion 160 protrudes upward from the cavity 111. An operator may easily grip the frame 130 by the protruding handle portion 160 in a state where the roll-type filter 10 is immersed in the cleaning solution C. FIGS. 6A to 6C are schematic diagrams illustrating a use state of the frame 130 according to an embodiment of the present disclosure. For convenience of description, the spacer 154 and the cleaning tank 110 are not illustrated in FIGS. 6A to 6C. The roll-type filter 10 supported by the frame 130 may be moved relatively to the cleaning solution C by rotating the frame 130 as illustrated in FIG. 6A, tilting the frame 130 as illustrated in FIG. 6B, or moving the frame 130 in a vertical direction as illustrated in FIG. 6C in a state where the frame 130 is gripped by the handle portion 160. Thus, the cleaning efficiency of the roll-type filter 10 may be improved.

In addition, the roll-type filter 10 may be easily transferred to the outside of the cleaning tank 110 by the handle portion 160. Even in a state where the cleaning solution C is discharged to the outside of the cleaning tank 110, the cleaning solution C may remain in the pores of the roll-type filter 10 before drying the roll-type filter 10. The weight of the roll-type filter 10 may be increased more than before the cleaning of the roll-type filter 10 due to the cleaning solution C remaining within the pores. Since such a roll-type filter 10 may be vulnerable to damage, it may be difficult to transfer the roll-type filter 10. However, in the current embodiment, the frame 130 itself is moved by the handle portion 160, and thus the roll-type filter 10 may be transferred without being damaged and without applying external force directly to the roll-type filter 10. The roll-type filter 10 may be naturally dried within the filter cleaning apparatus 1, but it may be transferred to a separate drying apparatus (not shown) so as to be forcibly dried.

The handle portion 160 may be detachably connected to the fixed portion 140.

Figure 7:
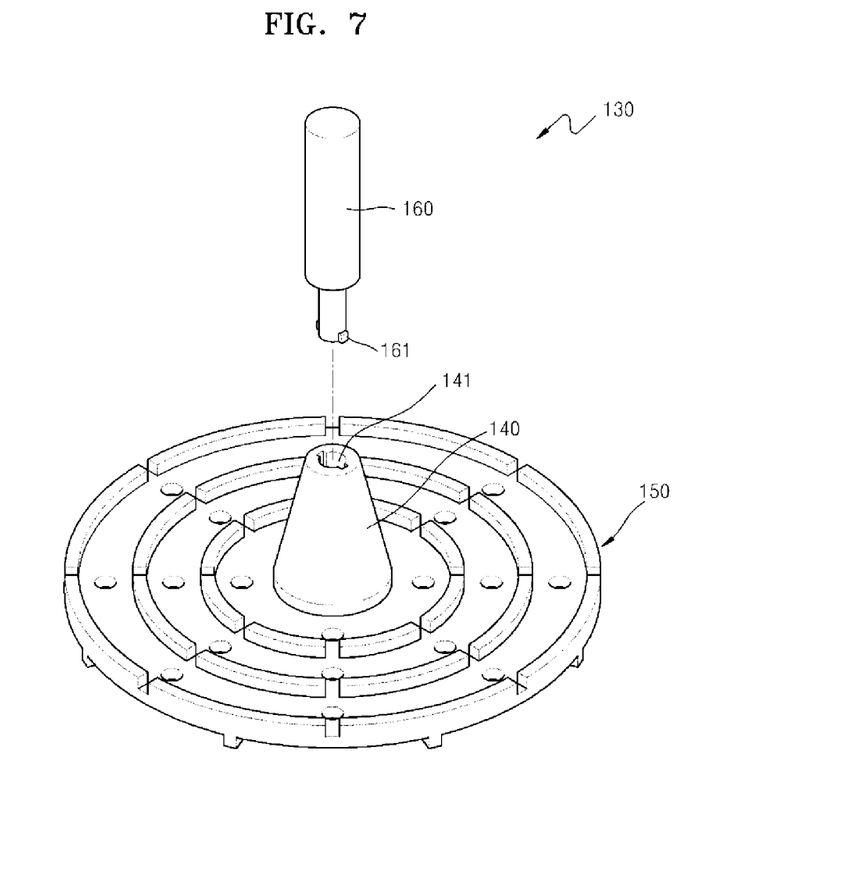
FIG. 7 is an exploded perspective view illustrating a state where a handle portion is detached from the frame of FIG. 4.

FIG. 7 is an exploded perspective view illustrating a state where the handle portion 160 is detached from the frame 130 of FIG. 4. Referring to FIG. 7, the handle portion 160 may be attached to the fixed portion 140 or detached from the fixed portion 140 as required. For example, when the roll-type filter 10 is moved to the separate drying apparatus by the handle portion 160, the handle portion 160 may be detached from the fixed portion 140 so that the handle portion 160 is not disturbed in the process of disposing the roll-type filter 10 within the drying apparatus.

The detachable connection between the handle portion 160 and the fixed portion 140 may be arranged in any suitable configuration.

Figure 8:
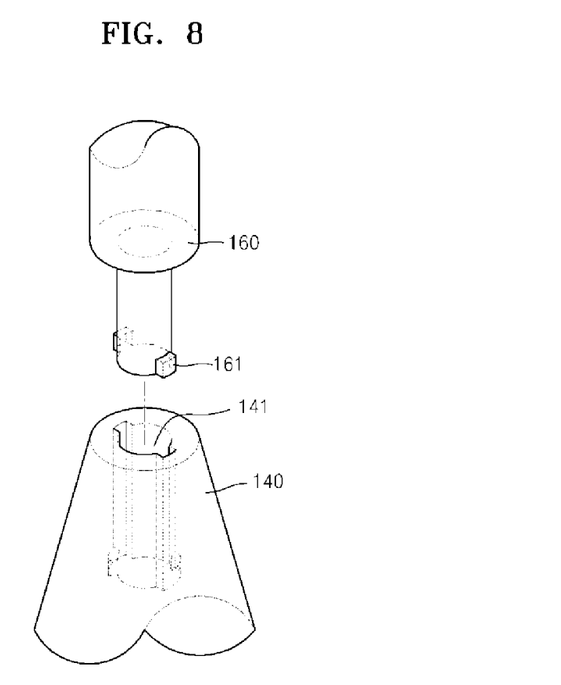
FIG. 8 is an enlarged partial perspective view of a connecting portion between the handle portion and a fixed portion in the frame of FIG. 4.

FIG. 8 is an enlarged partial perspective view of a connecting portion between the handle portion 160 and the fixed portion 140 in the frame 130 of FIG. 4. Referring to FIG. 8, as an example of the detachable connection between the handle portion 160 and the fixed portion 140, the handle portion 160 may include a locking member 161, and the fixed portion 140 may include an insertion hole 141 into which the locking member 161 may be inserted.

The fixed portion 140 may be detachably connected to the supporting portion 150. The fixed portion 140 may be attached to the supporting portion 150 and detached from the supporting portion 150 as required. Thus, various types of supporting portions 150 and fixed portions 140 may be connected to each other according to the diameter D1 of the roll-type filter 10 or the diameter of the hollow shaft 15. That is, compatibility may be improved. The detachable connection between the fixed portion 140 and the supporting portion 150 may be configured in any suitable manner. For example, the fixed portion 140 may be detachably connected to the supporting portion 150 in a manner similar to the structure illustrated in FIG. 8.

Hereinafter, reference will be made to FIGS. 1 and 2 to describe a process of cleaning the roll-type filter 10 by using the filter cleaning apparatus 1 having the above-mentioned configuration.

A first cleaning solution is injected into the filter cleaning apparatus 1 in which the frame 130—including the supporting portion 150, the fixed portion 140, and the handle portion 160—is disposed in the cavity 111 of the cleaning tank 110. At this time, the first cleaning solution may vary depending on a material of the roll-type filter 10 to be cleaned. For example, when the roll-type filter 10 is formed of glass fiber, hydrochloric acid (HCl) may be used.

The roll-type filter 10 is disposed in the filter cleaning apparatus 1 accommodating the first cleaning solution so as to be immersed in the first cleaning solution. At that time, in a state where the handle portion 160 exposed to the outside of the cleaning tank 110 is gripped, external force is applied to the filter cleaning apparatus 1 so as to move the frame 130 in a vertical direction, to rotate or tilt the frame 130. Thus, the roll-type filter 10 is moved relatively to the first cleaning solution, thereby improving the cleaning efficiency of the roll-type filter 10 through the first cleaning solution.

Next, the first cleaning solution is discharged to the outside of the cleaning tank 110 through the outlet 113, and then a second cleaning solution is injected into the cleaning tank 110. Since the diameter D2 of the cavity 111 is larger by approximately at least 5 cm than the diameter D1 of the roll-type filter 10, the second cleaning solution may be prevented from being directly poured in the roll-type filter 10 at the time of injection of the second cleaning solution. The injected second cleaning solution is supplied to the roll-type filter 10, and thus the first cleaning solution may be prevented from remaining in the pores of the roll-type filter 10. At this time, external force is applied to the handle portion 160, which is exposed to the outside of the cleaning tank 110, so as to vertically move, rotate, or tilt the frame 130. Thus, the roll-type filter 10 is moved relatively to the second cleaning solution, and thus the first cleaning solution remaining in the pores of the roll-type filter 10 may be effectively removed. The second cleaning solution may be a material having a higher volatility than the first cleaning solution. The second cleaning solution may be an organic material such as acetone.

The second cleaning solution is discharged to the outside of the cleaning tank 110 through the outlet 113, and then the roll-type filter 10 may be dried. The second cleaning solution may partially remain in the pores of the roll-type filter 10. However, when the second cleaning solution is a material with a volatility higher than that of the first cleaning solution, the second cleaning solution may be easily removed through drying. The roll-type filter 10 may be naturally or forcibly dried. When the roll-type filter 10 is forcibly dried, the roll-type filter 10 may be easily moved to an external drying apparatus (not shown) by using the handle portion 160 of the frame 130. For convenience of description, an example in which two types of cleaning solutions are used has been mainly described, but one cleaning solution or three or more types of cleaning solutions may be used as required.

The roll-type filter 10, having a good quality, from which foreign substances or electrolytes are removed, may be attained through the above-mentioned cleaning process including a drying process.

EXAMPLE 1

An experiment of actually cleaning the roll-type filter 10 was performed by using the filter cleaning apparatus 1 according to FIG. 2.

<Specifications of the Used Filter>

The roll-type filter 10 which is formed of glass fiber and has a length of 50 m when unwound was used.

<Experimental Conditions>

First cleaning solution and cleaning time: hydrochloric acid (HCl) solution of 0.5 mM/30 seconds.

Second cleaning solution and cleaning time: distilled water/5 minutes.

Third cleaning solution and cleaning time: acetone solution/2 hours.

Fourth cleaning solution and cleaning time: acetone solution/1 hour.

Drying: after drying for a predetermined period of time by using a fume hood, drying in an oven at a temperature of 60° C.

<Results of Experiment>

In order to ascertain whether the roll-type filter 10 is cleaned, human serum was passed through the roll-type filter 10 either before the roll-type filter 10 was cleaned ("Filter Before Cleaning") or after the roll-type filter 10 was cleaned ("Filter After Cleaning").The concentration of electrolytes was then measured. Roche Modular Evo was used for the measurement.

|  |  | $Na^+$ [mM] | $K^+$ [mM] | $Cl^-$ [mM] | $Ca^{2+}$ [mM] |
|---|---|---|---|---|---|
| Human Serum | | 148 | 4.2 | 97 | 10.5 |
| Filter Before Cleaning | | 151 | 4.2 | 102 | 11.4 |
| Filter After Cleaning | 1 m | 148 | 4.2 | 97 | 10.6 |
| | 10 m | 148 | 4.2 | 97 | 10.6 |
| | 19 m | 148 | 4.2 | 97 | 10.7 |
| | 28 m | 148 | 4.2 | 97 | 10.7 |
| | 37 m | 149 | 4.2 | 98 | 10.8 |
| | 46 m | 149 | 4.2 | 98 | 10.8 |

The human serum used in the experiment contained sodium ion ($Na^+$) of 148 mM, potassium ion ($K^+$) of 4.2 mM, chlorine ion ($Cl^-$) of 97 mM, and calcium ion ($Ca^{2+}$) of 10.5 mM at the beginning. After such human serum was passed through the roll-type filter 10 which had not been cleaned, the amounts of the sodium ion ($Na^+$), the potassium ion ($K^+$), the chlorine ion ($Cl^-$), and the calcium ion ($Ca^{2+}$) were 151 mM, 4.2 mM, 102 mM, and 11.4 mM, respectively. That is, the roll-type filter 10 which had not been cleaned itself contained concentrations of sodium ion ($Na^+$) of approximately 3 mM, chlorine ion ($Cl^-$) of approximately 5 mM, and calcium ion ($Ca^{2+}$) of approximately 0.9 mM.

After the cleaning was performed according to the experimental conditions whereby the roll-type filter 10 is disposed in the filter cleaning apparatus 1 of FIG. 2 and cleaned, the increase in sodium ion ($Na^+$), the chlorine ion ($Cl^-$), and the calcium ion ($Ca^{2+}$) concentrations was remarkably reduced in amount or was completely eliminated , as compared with serum passed through the roll-type filter 10 which had not been cleaned.

In addition, as a result of the measurement of the roll-type filter 10 after the cleaning at a total of six points thereof in units of 9 m, the sodium ion ($Na^+$), the chlorine ion ($Cl^-$), and the calcium ion ($Ca^{2+}$) which were contained in the roll-type filter 10 before the cleaning were remarkably reduced in the amount or were completely removed at all the six points. Thereafter, the whole length of the roll-type filter 10 was uniformly cleaned by the filter cleaning apparatus 1 according to the current embodiment. At this time, the roll-type filter 10 was not damaged.

Figure 9:
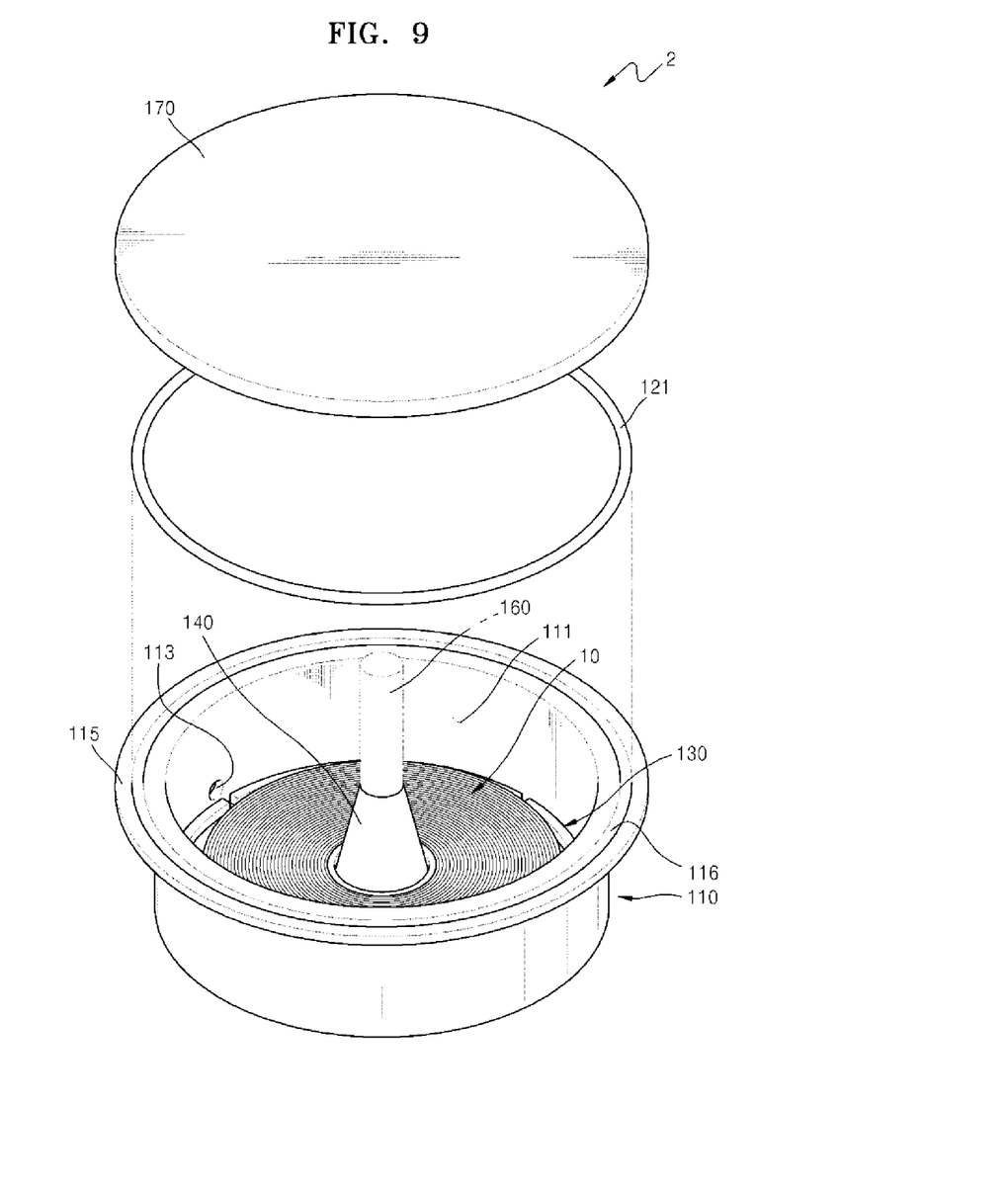
FIG. 9 is a schematic exploded perspective view of a filter cleaning apparatus according to another embodiment of the present disclosure.

FIG. 9 is a schematic exploded perspective view of a filter cleaning apparatus 2 according to another embodiment of the present disclosure. Referring to FIG. 9, the filter cleaning apparatus 2 may include a cleaning tank 110, a frame 130, and a cover 170. Here, the same components as the above-mentioned embodiments are denoted by the same reference numerals, and a description thereof will not be repeated.

The filter cleaning apparatus 2 according to the current embodiment may further include a cover 170 that is disposed above a cavity 111 of the cleaning tank 110, thereby preventing a cleaning solution from vaporizing to the outside of the cleaning tank 110. In particular, this may be more effective in a case where the cleaning solution is a material having high volatility, for example, acetone or ethanol.

An elastic member 121 having a ring shape may be disposed between the cover 170 and the cleaning tank 110. A groove 116 for accommodating the elastic member 121 may be formed in at least one of the cover 170 and the cleaning tank 110. In the filter cleaning apparatus 2 having the elastic member 121 disposed between the cover 170 and the cleaning tank 110, the inside of the cavity 111 may become a vacuum dried environment when a vacuum pump (not shown) is later connected to the outlet 113.

When the cover 170 is used, a handle portion 160 may be detached from a fixed portion 140. When the cover 170 is opened or is not used, the handle portion 160 may be attached to the fixed portion 140 and used.

Figure 10:
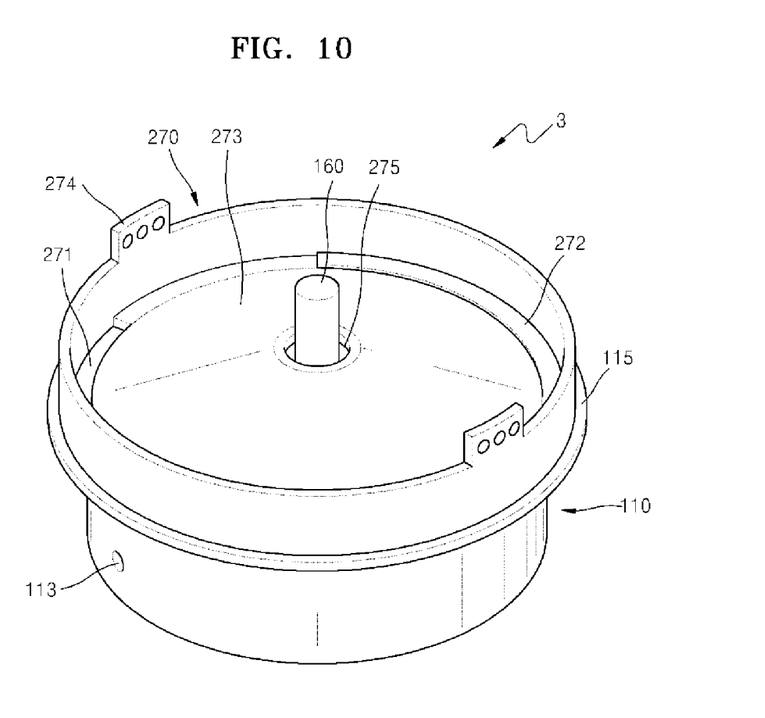
FIG. 10 is a schematic assembled perspective view of a filter cleaning apparatus according to another embodiment of the present disclosure.

FIG. 10 is a schematic assembled perspective view of a filter cleaning apparatus 3 according to another embodiment of the present disclosure. Referring to FIG. 10, the filter cleaning apparatus 3 may include a cleaning tank 110, a frame 130, and a cover 270. Here, the same components as the above-mentioned embodiments are denoted by the same reference numerals, and a description thereof will not be repeated.

The filter cleaning apparatus 3 according to the current embodiment may further include the cover 270 which is disposed over a cavity 111 of the cleaning tank 110. The cover 270 may be provided with a hole 271 along at least a portion of an edge of the cover, suitable for injecting a cleaning solution.

The cleaning solution is injected into the cleaning tank 110 through the hole 271 formed in the edge of the cover 270, and thus the cleaning solution may be prevented from being directly poured in a roll-type filter 10 in large quantities. This is because the roll-type filter 10 may be damaged when the cleaning solution is directly poured in the roll-type filter 10 in large quantities.

The cover 270 may include an inclined portion 273 that is sloped toward the hole 271 so that the cleaning solution poured from above the cover 270 may flow to the hole 271.

In addition, the cover 270 may further include an opening and closing portion 272 capable of selectively obstructing the hole 271. For example, the opening and closing portion 272 may be moved in the circumferential direction in a sliding manner so as to obstruct the hole 271.

Meanwhile, a holder portion 274 and a handle exposing portion 275 may be formed in the cover 270. The cover 270 may be easily gripped by the holder portion 274, and the handle portion 160 may be exposed through the handle exposing portion 275.

The exemplary embodiments regarding the filter cleaning apparatuses 1, 2, and 3 have been described so far and are illustrated in the accompanying drawings. However, it should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A filter cleaning apparatus for cleaning a roll-type filter, the apparatus comprising:
   (i) a cleaning tank provided with a cavity for accommodating a cleaning solution; and
   (ii) a frame that is separable from the cleaning tank and comprises a supporting portion for supporting weight of the roll-type filter and a fixed portion protruding from the supporting portion for fixing the roll-type filter,
   wherein the supporting portion comprises a circular base having a plurality of through holes through which the cleaning solution passes, and a plurality of supporting members for partially supporting a lower portion of the roll-type filter,
   the supporting members are separated from each other in a radial direction relative to the center of the circular base and protrude from the top surface of the circular base toward the roll-type filter, and each of the supporting members extends in a circumferential direction of the roll-type filter, and
   the supporting members comprise at least one first supporting member extending along the circular base in a circumferential direction of the circular base and having a first radius from the center of the circular base, and at least one second supporting member extending along the circular base in a circumferential direction of the circular base and having a second radius from the center of the circular base, the second radius being larger than the first radius,
   wherein at least one of the through holes is disposed between the at least one first supporting member and the at least one second supporting member.

2. The filter cleaning apparatus of claim 1, wherein the fixed portion of the frame is configured for insertion into a hollow shaft of a roll-type filter so as to fix the roll-type filter.

3. The filter cleaning apparatus of claim 1, wherein the frame further comprises a handle portion which protrudes outside of the cleaning tank.

4. The filter cleaning apparatus of claim 1, wherein a distance between the supporting members is approximately 5 mm to approximately 50 mm.

5. The filter cleaning apparatus of claim 1, wherein a protruding height of the supporting members is approximately 5 mm to approximately 10 mm.

6. The filter cleaning apparatus of claim 1, wherein a width of the supporting members is approximately 5 mm to approximately 10 mm.

7. The filter cleaning apparatus of claim 1, wherein the supporting members are disposed along the circumferential direction of the circular base so as to be separated from each other.

8. The filter cleaning apparatus of claim 1, wherein at least a portion of the frame is disposed within the cleaning tank, and at least one of the cleaning tank and the frame comprises a spacer so that a bottom surface of the cleaning tank and a lower surface of the supporting portion are separated from each other.

9. The filter cleaning apparatus of claim 1, wherein the cleaning tank further comprises an outlet for discharging the cleaning solution.

10. The filter cleaning apparatus of claim 2, wherein the fixed portion is detachably connected to the supporting portion.

11. The filter cleaning apparatus of claim 2, wherein the fixed portion comprises an upper region and a lower region, wherein the upper region is further from the cleaning tank than the lower region, and the diameter of the upper region is smaller than the diameter of the lower region.

12. The filter cleaning apparatus of claim 3, wherein the handle portion is detachably connected to the fixed portion.

13. The filter cleaning apparatus of claim 1, further comprising a cover which is disposed above the cavity.

14. The filter cleaning apparatus of claim 13, further comprising an elastic member having a ring shape which is disposed between the cover and the cleaning tank.

15. The filter cleaning apparatus of claim 13, wherein the cover is provided with a hole for injecting the cleaning solution in at least a portion of an edge of the cover.

16. The filter cleaning apparatus of claim 15, wherein the cover is provided with an opening and closing portion capable of obstructing the hole.

17. The filter cleaning apparatus of claim 15, wherein the cover has an inclined portion which is sloped toward the hole.

\* \* \* \* \*